United States Patent [19]

Rayudu

[11] Patent Number: 4,945,109

[45] Date of Patent: Jul. 31, 1990

[54] ESTER OF CARBAMIC ACID USEFUL AS A MICROBICIDE AND A PRESERVATIVE

[75] Inventor: S. Rao Rayudu, Germantown, Tenn.

[73] Assignee: Buckman Laboratories International, Inc., Memphis, Tenn.

[21] Appl. No.: 235,943

[22] Filed: Aug. 24, 1988

[51] Int. Cl.$^5$ ............................................. A01N 47/12
[52] U.S. Cl. ................................ 514/478; 8/94.1 R; 106/18.32; 252/403; 422/37; 427/440; 560/167
[58] Field of Search ................... 560/167; 514/478; 252/49.3, 49.5, 403; 422/37; 8/94.1 R; 106/18.32; 427/440

[56] References Cited

U.S. PATENT DOCUMENTS

| | | | |
|---|---|---|---|
| 2,814,637 | 11/1957 | Marshall et al. | 260/482 |
| 2,816,910 | 12/1957 | Junkmann et al. | 260/482 |
| 2,881,070 | 4/1959 | Pera | 92/3 |
| 3,660,499 | 5/1972 | Kobayashi et al. | 260/613 D |
| 3,923,870 | 12/1975 | Singer | 260/482 C |
| 4,259,350 | 3/1981 | Morisawa et al. | 424/308 |
| 4,323,602 | 4/1982 | Parker | 514/478 |
| 4,474,807 | 10/1984 | Gerhardt | 514/478 |
| 4,592,773 | 6/1986 | Tanaka et al. | 71/88 |
| 4,616,004 | 10/1986 | Edwards | 514/63 |
| 4,639,460 | 1/1987 | Rose | 514/369 |
| 4,639,541 | 1/1987 | Staiger et al. | 560/20 |
| 4,647,572 | 3/1987 | Inouye et al. | 514/381 |
| 4,661,632 | 4/1987 | Oeckl et al. | 564/217 |

FOREIGN PATENT DOCUMENTS 627647 9/1961 Canada .
39-10910 6/1964 Japan .
2140299A 11/1984 United Kingdom .

OTHER PUBLICATIONS

Chemical Abstract, vol. 105:225980f, 1986.
Chemical Abstract, vol. 81:169082m, 1984.
Thorn et al., "The Dithiocarbamates and Related Compounds," Elsevier Publishing Co., New York, 1962.
Rich et al., "Fungitoxicity of Carbamic Acid and Thiocarbamic Acid Esters," Connecticut Experiment Station Bulletin 639, New Haven, 1961.

*Primary Examiner*—Michael L. Shippen
*Attorney, Agent, or Firm*—Finnegan, Henderson, Farabow, Garrett & Dunner

[57] ABSTRACT

A novel ester of carbamic acid useful in controlling the growth and proliferation of microorganisms. The novel compound is

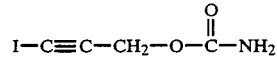

namely, 3-iodopropargyl ester of carbamic acid.

18 Claims, No Drawings

ESTER OF CARBAMIC ACID USEFUL AS A MICROBICIDE AND A PRESERVATIVE

BACKGROUND OF THE INVENTION

1. Field of the Invention

The present invention relates to novel 3-iodopropargyl ester of carbamic acid, and to use of the ester as a microbicide and preservative.

2. Description of Related Art

A large number of commercial, industrial, agricultural, and wood products are subject to microbiological attack which reduces or destroys their economic value. Examples of materials that may be subject to degradation are surface coatings, wood, agricultural seed, leather and plastics, including flexible plastics.

Examples of aqueous systems containing organic materials subject to attack are latexes, surfactants, dispersants, stabilizers, thickeners, adhesives, starches, waxes, proteins, emulsifying agents, detergents, cellulose products, and resins formulated in aqueous solutions, emulsions or suspensions. Such products frequently contain relatively large amounts of water.

The temperature at which these products are stored and their intrinsic characteristics make these products susceptible to the growth of microorganisms. These microorganisms can be introduced during the manufacturing of these products by exposure to air, tanks, pipes, equipment, and humans and/or during their use from multiple openings and reclosures of packaged products and by the introduction of contaminated objects to stir or remove material.

Microbiological degradation of aqueous systems containing organic materials may manifest itself in a variety of problems, such as loss of viscosity, gas formation, objectionable odors, decreased pH, emulsion breaking, color change, and gelling.

Another objectionable phenomenon occurring in industrial process systems involving water is slime formation. Slime consists of matted deposits of microorganisms, fibers and debris. It may be stringy, pasty, rubbery, tapioca-like, or hard, and it may have a characteristic odor that is different from that of the liquid suspensions in which it is formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeasts, and yeast-like organisms. Slime reduces yields in paper production and causes plugging and other problems in water systems.

Compounds containing an iodopropargyl group have shown fungicidal and bactericidal activity. U.S. Pat. No. 4,259,350 teaches the use of iodopropargyl esters of carboxylic acids and sulfonic acids as microbicides. U.S. Pat. No. 4,592,773 claims substituted propargyloxyacetonitrile derivatives as agricultural fungicides. U.S. Pat. No. 3,660,499 discloses aryl-3-iodopropargyl formals as fungicides. U.S. Pat. No. 4,639,460 discusses the fungicidal properties of N-(1-iodopropargyl)-thiazolidinones. U.S. Pat. No. 4,616,004 enumerates the uses of 1-iodopropargyl-3, 4-disubstituted-Δ²-1,2,4-triazolidin-5-ones as agricultural fungicides. U.S. Pat. No. 3,923,870 teaches the use of urethanes of 1-halogen substituted alkynes as fungicides, particularly when used in surface coating compositions such as paint formulations. These urethanes are prepared using organic isocyanates. Organic isocyanates have the unique disadvantage of being manufactured from phosgene, a dangerous and difficult chemical to handle. Once prepared, these organic isocyanates are difficult to store and handle because of their sensitivity to air and their propensity to react with water to produce hydrochloric acid fumes. Some of these isocyanates can also produce chronic health hazards. The present invention, as will be shown, uses inorganic cyanates which are relatively safe to handle.

Furthermore, the urethanes divulged in U.S. Pat. No. 3,923,870 differ from the compounds of present invention, in that, the former have an alkyl group of a 1–20 carbon chain attached to the nitrogen atom and the latter do not. In addition, these urethane compounds do not possess effective bactericidal utility.

It is an object of the present invention to provide a 3-iodopropargyl ester of carbamic acid having effective batericidal utility.

It is another object to provide a method for inhibiting the growth of microorganisms in aqueous systems.

It is still another object to provide a method for inhibiting the formation of slime in an aqueous liquid.

It is a further object of the present invention to provide a method for inhibiting the growth of microorganisms on a substance susceptible to deterioration or disfiguration by microorganisms.

Additional objects and advantages of the invention will be set forth in the description which follows, and in part will be apparent from the description, or may be learned by pratice of the invention. The objects and advantages of the invention may be realized and obtained by means of the combinations particularly pointed out in the appended claims.

SUMMARY OF THE INVENTION

To achieve the foregoing objects, and in accordance with the purposes of the invention as embodied and broadly described herein, there is provided a novel ester of carbamic acid useful in controlling the growth and proliferation of microorganisms.

The novel compound is

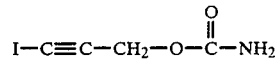

namely, 3-iodopropargyl ester of carbamic acid, which can also be referred to as carbamic acid, 3 iodopropargyl ester.

DETAILED DESCRIPTION OF THE INVENTION

The novel 3-iodopropargyl ester of carbamic acid is prepared by reacting iodopropargyl alcohol with an alkali metal cyanate, preferably potassium or sodium cyanate, usually in the presence of a catalyst.

The iodopropargyl alcohol can be prepared by methods known in the literature. The preferable method is to react potassium or sodium iodide with propargyl alcohol in the presence of sodium hypochlorite.

Alcohols can be reacted with sodium cyanate in an organic solvent, preferably methylene chloride, and this reaction can be catalyzed by different organic acid catalysts, preferably trifluoroacetic acid or trichloroacetic acid, as described in U.S. Pat. No. 2,814,637. The ratio of iodopropargyl alcohol to sodium cyanate is stoichiometric, even though a slight molar excess of one or the other reactant can be used to produce the desired ester of carbamic acid.

The temperatures at which these reactions can be run generally range from 0° C. to 100° C., preferably from 30° C. to 40° C. These reactions are generally stirred for 2 to 16 hours, preferably for 6 to 10 hours.

After the reaction is completed, as shown by gas chromatographic analysis, the reaction product can be worked up to yield the desired iodopropargyl ester in several different ways. One procedure is to filter out the solids, washing the solids with organic solvent, combining the organic extracts, washing these extracts with water and ultimately evaporating the organic solvent to yield the 3-iodopropargyl ester of carbamic acid.

It is not intended to limit the preparation of this compound to the exact process or steps described above. Any equivalent procedure which yields the same end product may be used.

This novel iodopropargyl ester of carbamic acid can be used in a method for inhibiting the growth of microorganisms in an aqueous system which comprises adding to the system the iodopropargyl ester in an amount effective to inhibit the growth of the microorganisms. Representative aqueous systems include aqueous solutions, emulsions and suspensions. Specific systems include a water-based paint and a metalworking fluid.

The iodopropargyl ester of the present invention can also be used in a method for inhibiting the formation of slime in an aqueous liquid, which comprises adding to the liquid the iodopropargyl ester in an amount effective to prevent the formation of slime. This method is effective in aqueous liquids such as a pulp slurry or liquids contained in a water cooling device.

A further use of the compound of the present invention resides in a method for inhibiting the growth of microorganisms on a substance susceptible to deterioration or disfiguration by microorganisms, which comprises applying or admixing with the substance the iodopropargyl ester in an amount effective to prevent the growth of the microorganisms. This method is effective on substances such as wood, paint-film, leather, flexible plastic and the like. The microorganisms which are prevented from growing may include fungi.

The compound of the present invention has a number of advantages over the microbicides hitherto available. It is an excellent microbicide to be used for both preservation of paint while in the can and after application on the painted surface. It is hydrolytically stable over a wide pH range (3-11) and can be used in both latex and oil-based systems. It is soluble in many solvents, and may therefore be readily diluted for convenience of use. Its compatability, low color, and efficiency makes it advantageous for use as a microbicide in plastic, and for impregnation in or application on the surface of wood, paper, cloth or other materials.

This compound may, of course, be applied in various ways—incorporated into a coating or composition, applied as dust by mixing with powdered diluents, dissolved in a solvent, or emulsified into water and then dispersed into a non-solvent. The particular application desired will generally dictate the method of use.

The effective amount or percentage of active compound necessary to achieve the desired result will vary somewhat depending on the substrate to be protected, the conditions for fungal growth, and the degree of protection desired. The concentration of the compound of the present invention generally ranges from about 0.0001% to 4% (w/w); preferably 0.0001% to 0.2%, and more preferably 0.0005% to 0.0050% in the composition applied. With aqueous systems, a preferred effective amount of active compound ranges from about 20 to 5000 parts per million, and more preferably, from about 250 to 2000 parts per million of the aqueous system. The amount of 3-iodopropargyl ester of carbamic acid effective to prevent the formation of slime in an aqueous liquid preferably ranges from about 1 to 200 parts per million, and more preferably, from about 5 to 25 parts per million of the aqueous liquid.

To illustrate the nature of invention, the following examples are given. It should be understood, however, that the invention is not to be limited to the specific conditions or details set forth in these examples.

EXAMPLE 1

To a solution of 18.2 g (0.1 mole) of iodopropargyl alcohol in 60 ml of methylene chloride in a 250 ml round-bottom flask was added 13.0 g (0.2 mole) of powdered sodium cyanate. To the above, well-stirred solution, 32.7 g (0.2 mole) of trichloroacetic acid was added and the mixture was stirred overnight. The resulting reaction mixture was filtered and the precipitate was washed with 40 ml of methylene chloride. The filtrate plus the methylene chloride wash were washed with one 50 ml portion of saturated sodium bicarbonate; and two 50 ml portions of water; dried over anhydrous magnesium sulfate; and evaporated in vacuo. The resulting off-white solid was purified by column chromatography using a 70:30 mixture of hexane and ethyl acetate. The purified iodopropargyl ester of carbamic acid is a solid with a melting point of 85°-87° C. and showed typical absorptions for amino, carbonyl and acetylenic functional groups in infrared spectroscopy. An elemental analysis of this product gave the following results in duplicate tests:

TABLE I

| Element | % Theoretical | % Found I | % Found II |
|---------|---------------|-----------|------------|
| C | 21.3 | 21.2 | 21.1 |
| H | 1.8 | 1.8 | 1.8 |
| I | 56.4 | 56.2 | 56.0 |
| N | 6.2 | 6.1 | 6.1 |

EXAMPLE 2

The preservative effectiveness of the compound prepared in Example 1 was determined in a freshly prepared water-based paint formulated with titanium dioxide and calcium carbonate as pigments, an acrylic resin emulsion, dispersants, and hydroxyethyl cellulose as a thickener. The pH of this paint was approximately 9.0. The test was conducted as follows:

3-Iodopropargyl ester of carbamic acid wa added to the completed acrylic latex paint at levels ranging from 250 to 2000 parts per million parts of the paint. One hundred gram samples of the test paint were inoculated weekly in a ten week challenge test with 1.0 milliliter of paint containing Pseudomonas aeruginosa at a level of approximately $1.5 \times 10^6$ organisms per milliliter. After vigorous shaking, the inoculated paint was incubated at 28° C. The test paints were streaked onto nutrient agar 24, 48, and 168 hours after inoculation. The streaked plates were incubated at 37° C. and examined for bacterial growth after 48 hours. Table II represents the final data accumulated from a ten week challenge test with paints containing 250 to 2000 parts of 3-iodopropargyl ester of carbamic acid per million parts of paint. The efficacy of the compound of present invention was compared to that of 3-iodopropargyl-n-butyl-carbamate, a commercially available paint preservative, described in U.S. Pat. No. 3,923,870.

TABLE II

| Concentration of Product (ppm) | 3-Iodopropargyl ester of Carbamic acid | | | 3-Iodopropargyl-n-butylcarbamate | | |
|---|---|---|---|---|---|---|
| | 24th | 48th | 168th | 24th | 48th | 168th |
| 0 (control) | 3 | 3 | 3 | 3 | 3 | 3 |
| 250 | 0 | 0 | 0 | 3 | 3 | 3 |
| 500 | 0 | 0 | 0 | 3 | 3 | 3 |
| 1000 | 0 | 0 | 0 | 3 | 3 | 3 |
| 2000 | 0 | 0 | 0 | 3 | 3 | 3 |

*Key: 0 = No growth
1 = 1 colony
2 = 2 to 10 colonies
3 = over 10 colonies

EXAMPLE 3

The compound of the present invention was tested by the pulp substrate method described in detail in U.S. Pat. No. 2,881,070 at column 5, beginning at line 12 and extending to column 6, line 53. U.S. Pat. No. 2,881,070 is specifically incorporated by reference herein. As set forth therein, a percentage kill of 80% or higher represents an extremely useful composition, and it does not follow that higher kills are necessarily better or more desirable. The tests utilized *Enterobacter aerogenes* and pulp substrates that had been buffered at pH 6.0 and 8.0. The results are tabulated in Table III.

TABLE III

Percent Kill of *Enterobacter aerogenes* in a pulp substrate at pH 6.0 and 8.0 after 18 hours of contact with 3-iodopropargl ester of carbamic acid.

| Concentration in ppm | pH 6 | pH 8 |
|---|---|---|
| 1 | 0 | 58 |
| 5 | 55 | 97 |
| 10 | 100 | 100 |
| 25 | 100 | 100 |
| 50 | 100 | 100 |

EXAMPLE 4

The growth inhibiting activity of carbamic acid, 3-iodopropargyl ester on the fungus *Aspergillus niger* was evaluated. A variation of the pulp substrate method of Example 3 was used.

When fungi are used as test organisms, the pulp-substrate test method is modified to permit the growth of these microorganisms. The pulp substrate comprises an aqueous slurry of spruce groundwood containing 1 percent by weight (dry basis) of wood fibers enriched by the addition of 0.26 percent of sodium nitrate and 0.64 percent of maltose (technical grade). Forty gram portions of the enriched groundwood pulp slurry were added to 250 ml Pyrex Erlenmeyer flasks fitted with loose metal caps and then sterilized. Each of the following substances was then added to the flasks in the order listed:

(1) Sterile, demineralized water as required in each individual case was added to bring the total weight of the contents of each flask to 50 grams, after allowing for all subsequent additions specified hereinafter (including inoculation with the aqueous suspension of spores and-/or mycelial fragments of the test fungus).

(2) One milliliter of a 2.0 percent by weight sterile solution of rosin size. Rosin size is the pasty sodium soap of rosin containing approximately 20 to 30 percent free rosin and 30 percent water. A suitable rosin size is that known as rosin size 70D made by Papermakers' Chemical Department, Hercules Inc., Kalamazoo, Mich.

(3) A solution of the toxicant or control agent to be evaulated in each test, to give the concentration desired in parts per million by weight.

(4) A sterile solution of buffer salts to adjust the substrate to a pH of 4.5 to 5.0, prepared from 0.2M solutions of potassium acid phthalate and sodium hydroxide.

(5) Inoculum consisting of 1 milliliter of an aqueous suspension of spores and/or mycelial fragments of the test organism. *Aspergillus niger* is the test fungus which was used for these tests.

The buffer mixtures were prepared according to the procedures set forth in U.S. Pat. No. 2,881,070.

After the inoculant suspensions of the test fungi were added, the flasks were incubated at a temperature of 30±1° C. for a period adequate for growth to occur in the controls (portions of inoculated pulp substrate which contained no toxicant). The customary periods of observation were after 7 and 14 days. Growth was recorded after each period on the basis of the following key:
4 = excellent
3 = good
2 = poor
1 = very poor, scant, questionable
0 = no growth
The results are summarized in Table IV.

TABLE IV

Inhibition of *Aspergillus niger* by carbamic acid, 3-iodopropargyl ester

| Concentrate (ppm) | Results After 14 Days |
|---|---|
| 0.5 | 4 |
| 1.0 | 0 |
| 2.0 | 0 |
| 4.0 | 0 |
| 5.0 | 0 |
| 10.0 | 0 |
| 25.0 | 0 |

EXAMPLE 5

A standard method for resistance to growth of mold on the surface of interior coatings in an environmental chamber, ASTM method D3273-86, was used to determine the effectiveness of 3-iodopropargyl ester of carbamic acid.

Treatments were prepared by dissolving 2.0 g of the iodopropargyl ester in 10 ml of acetone/methanol. Two types of paint were used, namely, an alkyd (self-priming white with Beckasol 296-70) and a latex (self-priming, alkyd modified acrylic paint). To 100 gram samples of each paint was added 2.5, 1.25, 0.625, 0.312 or 0.156 ml to achieve 0.5%, 0.25%, 0.125%, 0.062% or 0.031% active ingredient (w/w), respectively. Each sample was shaken vigorously for 5 minutes using a standard paint shaker.

Blocks of drywall having two inch by four inch dimensions were painted on the front surface and on all edges with two coats of the respective treatments. After drying, the back side was painted with one coat of clear latex. A hole was drilled half-way through the block at one end, and duplicate blocks per treatment were hung in an environmental chamber.

The aggressive nature of the interior of the chamber was developed by inoculating trays of moist potting soil with active cultures of *Aspergillus* sp., *Aureobasidium* sp., *Trichoderma* sp., *Penicillium* sp., and *Chaetomium* sp. The chamber was maintained at 100 percent relative humidity and 32° C. Final observations were made after four weeks (for latex blocks) or eight weeks (for alkyd blocks).

Subjective scores were assigned based on:
10=no mold growth
9=very slight mold growth
8=slight growth
7,6=slight to medium growth
5=failure (extensive growth)
The results are tabulated in Table V.

TABLE V

Growth of mold on the surface of interior coatings preserved with carbamic acid, 3-iodopropagyl ester in an environmental chamber.

| Treatment Level (% by Wt) | Latex | Alkyd |
|---|---|---|
| 0 (Control) | 5 | 5 |
| 0.031 | 5 | 5 |
| 0.062 | 9.5 | 5 |
| 0.125 | 5 | 8 |
| 0.25 | 6 | 10 |
| 0.50 | 10 | 10 |

EXAMPLE 6

The effect of 3-iodopropargyl ester of carbamic acid against wood rotting and wood staining fungi was evaluated using an accelerated laboratory test for evaluating toxicity of fungicides for lumber (Cserjesi, A. J. and Roff, J. W. 1970 in *Materials Research Standard* 10(3): 18-19, 59-60).

At a concentration of 1000 ppm, the compound of the present invention controlled both wood rotting and wood staining fungi, whereas at 250 ppm it provided 57% control.

EXAMPLE 7

The compound of the present invention was tested as a preservative in metalworking fluids using Standard Method for the Evaluation of Antimicrobial Agents in Aqueous Metalworking Fluids (ASTM method E686-80).

This ASTM test is a multiple challenge test designed to simulate industrial conditions. The biocide was added to 450 ml aliquots of synthetic or soluble oil metalworking fluid.

The metalworking fluid samples were then inoculated with 50 ml of a mixed microbial culture and aerated on a specific time cycle. The cycle is composed of five days of aeration followed by two days without aeration, which simulates an industrial work schedule. The microorganisms used in the metalworking fluid inoculum included:
(1) "Wild" fungi and bacteria obtained from a spoiled industrial fluid
(2) *Staphylococcus aureus*
(3) *Pseudomonas aeruginosa*
(4) *Klebsiella pneumoniae*
(5) *Escherichia coli*

Every week, for a minimum of 6 weeks or until the test failed, the metalworking fluid samples were measured for microbial growth. This was done by counting the bacteria and fungi using standard plate-counting techniques. The bacteria were incubated on trypticase soy agar and the fungi on saboraud dextrose agar prior to counting.

If by the end of six weeks the microbial count in the synthetic fluid remains below $1.0 \times 10^4$ colony forming units (cfu) per ml, it is considered adequately preserved.

It was found that 20 parts of carbamic acid, 3-iodopropargyl ester, adequately preserved one million parts of both synthetic and soluble oil metalworking fluids.

Having thus described the invention in rather full detail it will be understood that such detail need not be strictly adhered to but that further changes and modifications may suggest themselves to one skilled in the art, all falling within the scope of the invention as defined by the claims.

What is claimed is:
1. A compound having the formula:

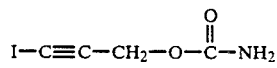

2. A method for inhibiting the growth of microorganisms in an aqueous system comprising the step of adding to said system the compound of claim 1 in an amount effective to inhibit the growth of said microorganisms.

3. The method of claim 2, wherein said effective amount is from 20 to 5000 parts per million of said aqueous system.

4. The method of claim 3, wherein said effective amount is from 250 to 2000 parts per million of said aqueous system.

5. The method of claim 2, wherein said aqueous system is selected from a group consisting of aqueous solutions, emulsions and suspensions.

6. The method of claim 2, wherein said aqueous system is a water-based paint.

7. The method of claim 2, wherein said aqueous system is a metalworking fluid.

8. A method for inhibiting the formation of slime in an aqueous liquid, comprising the step of adding to said liquid the compound of claim 1 in an amount effective to prevent the formation of slime.

9. The method of claim 8, wherein said effective amount is from 1 to 200 parts per million of said aqueous liquid.

10. The method of claim 9, wherein said effective amount is from 5 to 25 parts per million of said aqueous liquid.

11. The method of claim 8, wherein said aqueous liquid is a pulp slurry.

12. The method of claim 8, wherein said aqueous liquid is contained in a water cooling device.

13. A method for inhibiting the growth of microorganisms on a substance susceptible to deterioration or disfiguration by microorganisms comprising the step of applying to or admixing with said substance the compound of claim 1 in an amount effective to prevent the growth of said microorganisms.

14. The method of claim 13, wherein said substance is wood.

15. The method of claim 13, wherein said substance is paint-film.

16. The method of claim 13, wherein said substance is leather.

17. The method of claim 13, wherein said microorganisms are fungi.

18. The method of claim 13, wherein said substance is a flexible plastic.

* * * * *